US00PP28818P3

(12) United States Plant Patent
Beekenkamp

(10) Patent No.: US PP28,818 P3
(45) Date of Patent: Dec. 26, 2017

(54) ***BEGONIA* PLANT NAMED 'BKPBECRM'**

(50) Latin Name: *Begonia×hiemalis*
Varietal Denomination: BKPBECRM

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 16 days.

(21) Appl. No.: 14/999,403

(22) Filed: May 3, 2016

(65) Prior Publication Data

US 2017/0325388 P1 Nov. 9, 2017

(51) Int. Cl.
*A01H 5/02* (2006.01)

(52) U.S. Cl.
USPC ..... Plt./349

(58) Field of Classification Search
USPC ..... Plt./349
See application file for complete search history.

*Primary Examiner* — June Hwu
(74) *Attorney, Agent, or Firm* — C. A. Whealy

(57) ABSTRACT

A new and distinct cultivar of *Begonia* plant named 'BKPBECRM', characterized by its broadly upright to outwardly spreading and mounded plant habit; sturdy plants with freely basal branching habit; dark green-colored leaves; uniform and freely flowering habit; and single-type female flowers and fully double male flowers that are dark red in color.

2 Drawing Sheets

Botanical designation: *Begonia×hiemalis.*
Cultivar denomination: 'BKPBECRM'.

CROSS-REFERENCED TO CLOSELY-RELATED APPLICATIONS

Title: *Begonia* Plant Named 'BKPBECLR'
Applicant: Annie Cornelia Beekenkamp
Filed: Concurrently with the instant application

BACKGROUND OF THE INVENTION

The present invention relates to a new and distinct cultivar of *Begonia* plant, botanically known as *Begonia×hiemalis*, commercially referred to as Elatior *Begonia* and hereinafter referred to by the name 'BKPBECRM'.

The new *Begonia* plant is a product of a planned breeding program conducted by the Inventor in Maasdijk, The Netherlands. The objective of the breeding program was to develop new freely branching and freely flowering *Begonia* plants with attractive flowers.

The new *Begonia* plant originated from a cross-pollination made by the Inventor in March, 2013 of a proprietary selection of *Begonia×hiemalis* identified as code number 6900484, not patented, as the female, or seed, parent with a proprietary selection of *Begonia×hiemalis* identified as code number 6500604, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in November, 2013.

Asexual reproduction of the new *Begonia* plant by vegetative tip cuttings in a controlled greenhouse environment in Maasdijk, The Netherlands since February, 2014 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBECRM'. These characteristics in combination distinguish 'BKPBECRM' as a new and distinct *Begonia* plant:

1. Broadly upright to outwardly spreading and mounded plant habit.
2. Sturdy plants with freely basal branching habit.
3. Dark green-colored leaves.
4. Uniform and freely flowering habit.
5. Single-type female flowers and fully double male flowers that are dark red in color.

Plants of the new *Begonia* can be compared to plants of the female parent selection. Plants of the new *Begonia* differ primarily from plants of the female parent selection in the following characteristics:

1. Plants of the new *Begonia* and the female parent selection differ in leaf texture as plants of the female parent selection have pubescent leaves.
2. Plants of the new *Begonia* and the female parent selection differ in flower color as plants of the female parent selection have orange yellow-colored flowers.

Plants of the new *Begonia* can be compared to plants of the male parent selection. Plants of the new *Begonia* differ primarily from plants of the male parent selection in the following characteristics:

1. Plants of the new *Begonia* and the male parent selection differ in flower form as plants of the male parent selection only have single-type flowers.
2. Plants of the new *Begonia* and the male parent selection differ in flower color as plants of the male parent selection have pale pink-colored flowers.

Plants of the new *Begonia* can be compared to plants of the *Begonia×hiemalis* 'BKPBECLR', disclosed in a U.S. Plant patent application Ser. No. 14/999,404 filed concurrently. Plants of the new *Begonia* differ from plants of 'BKPBECLR' in the following characteristics:

1. Plants of the new *Begonia* are shorter than plants of 'BKPBECLR'.
2. Plants of the new *Begonia* and 'BKPBECLR' differ in leaf color as plants of 'BKPBECLR' have very dark-colored leaves.
3. Male flowers of plants of the new *Begonia* have more tepaloids than male flowers of plants of 'BKPBECLR'.

Plants of the new *Begonia* can also be compared to plants of the *Begonia×hiemalis* 'Baladin', not patented. In side-by-side comparisons, plants of the new *Begonia* differ from plants of 'Baladin' in the following characteristics:

1. Plants of the new *Begonia* are more vigorous than plants of 'Baladin'.
2. Plants of the new *Begonia* are more freely branching than plants of 'Baladin'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBECRM' grown in a container.

The photograph on the second sheet are close-up views of upper and lower surfaces of typical fully developed male flowers and leaves of 'BKPBECRM'.

DETAILED BOTANICAL DESCRIPTION

Plants used for the aforementioned photographs and following observations and measurements were grown during the winter in 12-cm containers in a glass-covered greenhouse in Maasdijk, The Netherlands. During the production of the plants, day and night temperatures ranged from 19° to 21° C. Plants were ten weeks old when the photographs and the description were taken. In the following description, color references are made to The Royal Horticultural Society Colour Chart, 2015 Edition, except where general terms of ordinary dictionary significance are used.

Botanical classification: *Begonia×hiemalis* 'BKPBECRM'.

Parentage:

*Female, or seed, parent*.—Proprietary selection of *Begonia×hiemalis* identified as code number 6900484, not patented.

*Male, or pollen, parent*.—Proprietary selection of *Begonia×hiemalis* identified as code number 6500604, not patented.

Propagation:

*Type*.—By vegetative tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; typically brown in color, actual color of the roots is dependent on substrate composition, water quality, fertilizer type and formulation, substrate temperature and physiological age of roots; plants of the new *Begonia* have not been observed to form tubers.

*Rooting habit*.—Freely branching habit; dense.

Plant description:

*Plant and growth habit*.—Broadly upright to outwardly spreading and mounded plant habit; plant shape flattened globular; moderately vigorous growth habit; moderate growth rate.

*Plant height, soil level to top of foliar plane*.—About 18.7 cm.

*Plant height, soil level to top of floral plane*.—About 20.4 cm.

*Plant width*.—About 35.1 cm.

*Lateral branch description*.—Branching habit: Freely branching habit with about four basal branches developing per plant; each basal branch with about three lateral branches; pinching is not required. Length: About 12.3 cm. Diameter: About 9 mm. Internode length: About 2.1 cm. Strength: Moderately strong. Aspect: About 35° from vertical. Texture and luster: Sparsely pubescent; glossy. Color, developing: Close to 170A. Color, fully developed: Close to 152A.

*Leaf description*.—Arrangement: Alternate, simple. Length: About 12.6 cm. Width: About 9.7 cm. Shape: Ovate. Apex: Acute. Base: Oblique, moderately imbricate. Margin: Crenate to serrulate; strongly undulate. Texture and luster, upper surface: Glabrous; slightly velvety; moderately glossy. Texture and luster, lower surface: Sparsely pubescent along veins; moderately glossy. Venation pattern: Laciniate. Color: Developing leaves, upper surface: Darker than between NN137A and 147A; narrow margin, close to 183A. Developing leaves, lower surface: Close to 147B; narrow margin, close to 183A. Fully expanded leaves, upper surface: Darker than between 147A and N189A; narrow margin, close to 178B; venation, close to 144A. Fully expanded leaves, lower surface: Close to 148B; narrow margin, close to 178B; venation, close to 144A. Petioles: Length: About 5.2 cm. Diameter: About 5 mm. Texture and luster, upper and lower surfaces: Moderately pubescent; moderately glossy. Color, upper and lower surfaces: Close to 166B; distally, close to 181A to 181B. Stipules: Quantity per leaf: Two. Length: About 1.1 cm. Width: About 1.3 cm. Shape: Broadly ovate. Apex: Obtuse. Base: Broadly cuneate. Margins: Entire. Color, upper and lower surfaces: Close to 144C; towards the margins, tinged with close to 180C to 180D.

Flower description:

*Flowering habit*.—Rotate single-type female flowers and fully double male flowers arranged in axillary compound cymes; freely flowering habit with about four flowers per cyme and about 140 flowers developing per plant; flowers face upright to outwardly.

*Fragrance*.—None detected.

*Natural flowering season*.—Long flowering period, plants flower freely and continuously from spring into the autumn in The Netherlands; during the winter in a greenhouse, plants begin flowering about 46 days after exposure to photoinductive treatments.

*Postproduction longevity*.—Individual flowers last about ten days on the plant; flowers not persistent; plants maintain good substance for about 20 to 30 days in an interior environment.

*Inflorescence height*.—About 6.3 cm.

*Inflorescence diameter*.—About 8.1 cm.

*Flower buds*.—Length: About 2.1 cm. Diameter, flattened: About 2 cm. Shape: Broadly obovate to roughly circular; flattened. Texture and luster: Glabrous, velvety; very slightly glossy. Color: Close to 42B to 42C.

*Female flowers*.—Diameter: About 5.1 cm. Depth: About 2.6 cm. Tepals: Quantity and arrangement: Five per flower, arranged in two whorls. Length: About 3.4 cm. Width: About 3.5 cm. Shape: Broadly obovate to roughly reniform. Apex: Rounded. Base: Reniform. Margin: Entire. Texture and luster, upper surface: Glabrous; velvety; matte. Texture and luster, lower surface: Glabrous; moderately velvety; matte to slightly glossy. Color: When opening, upper surface: Close to N45A. When opening, lower surface: Close to between 42A and 45A. Fully opened, upper surface: Close to 45B; color does not fade with development. Fully opened, lower surface: Close to 45A; color does not fade with development. Tepaloids: None observed on female flowers.

*Male flowers*.—Diameter: About 5.1 cm. Depth: About 2.6 cm. Tepals: Quantity and arrangement: Two per flower, opposite. Length: About 3.4 cm. Width: About 3.5 cm. Shape: Broadly obovate to roughly reniform. Apex: Rounded. Base: Reniform. Margin: Entire. Texture and luster, upper surface: Glabrous; velvety; matte. Texture and luster, lower surface: Glabrous; moderately velvety; matte to slightly glossy. Color: When opening, upper surface: Close to N45A. When opening, lower surface: Close to between 42A and 45A. Fully opened, upper surface: Close to 45B; color does not fade with development. Fully opened, lower surface: Close to 45A; color does not fade with development. Tepaloids: Quantity and arrangement: About 30 per flower, arranged in multiple whorls at the center of the flower. Length: Variable, about 1.1 cm to 2.4 cm. Width: Variable, about 0.9 cm to 2.6 cm. Shape: Broadly obovate. Apex: Rounded. Base: Broadly attenuate. Margin: Entire. Texture and luster, upper and lower surfaces: Glabrous; velvety; matte. Color: When opening, upper surface: Close to 45B. When opening, lower surface: Close to 45A to 45B. Fully opened, upper surface: Close to 45A; color does not fade with development. Fully opened, lower surface: Close to 44A; color does not fade with development.

*Peduncles*.—Length: About 4.5 cm. Diameter: About 4 mm. Angle: About 35° from lateral branch axis. Strength: Moderately strong; flexible. Texture and luster: Glabrous; moderately glossy. Color: Close to 166B to 166C tinged with close to 152A.

*Pedicels*.—Length: About 1.6 cm. Diameter: About 2 mm. Angle: About 35° from the peduncle axis. Strength: Moderately strong; flexible, bending with the weight of the flowers. Texture and luster: Glabrous; glossy. Color: Close to 179A to 179B.

*Flower bracts*.—Quantity and arrangement: Two per flower, opposite. Length: About 1.8 cm. Width: About 1.9 cm. Shape: Roughly reniform. Apex: Broadly acute. Base: Reniform. Margin: Entire. Texture and luster, upper and lower surfaces: Glabrous; matte. Color, upper and lower surfaces: Close to 146C; towards the apex, close to 179B.

*Reproductive organs*.—Stamens: None observed on male flowers, all structures transformed into tepaloids. Pistils: Present only on female flowers. Quantity per flower: Three. Length: About 7 mm. Style length: About 2 mm. Style color: Close to 150C to 150D. Stigma diameter: About 4.5 mm. Stigma shape: Cleft. Stigma color: Close to 23A. Ovary color: Close to 179A. Seeds and fruits: Seed and fruit development have not been observed on plants of the new *Begonia*.

Pathogen & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKPBE-CRM' as illustrated and described.

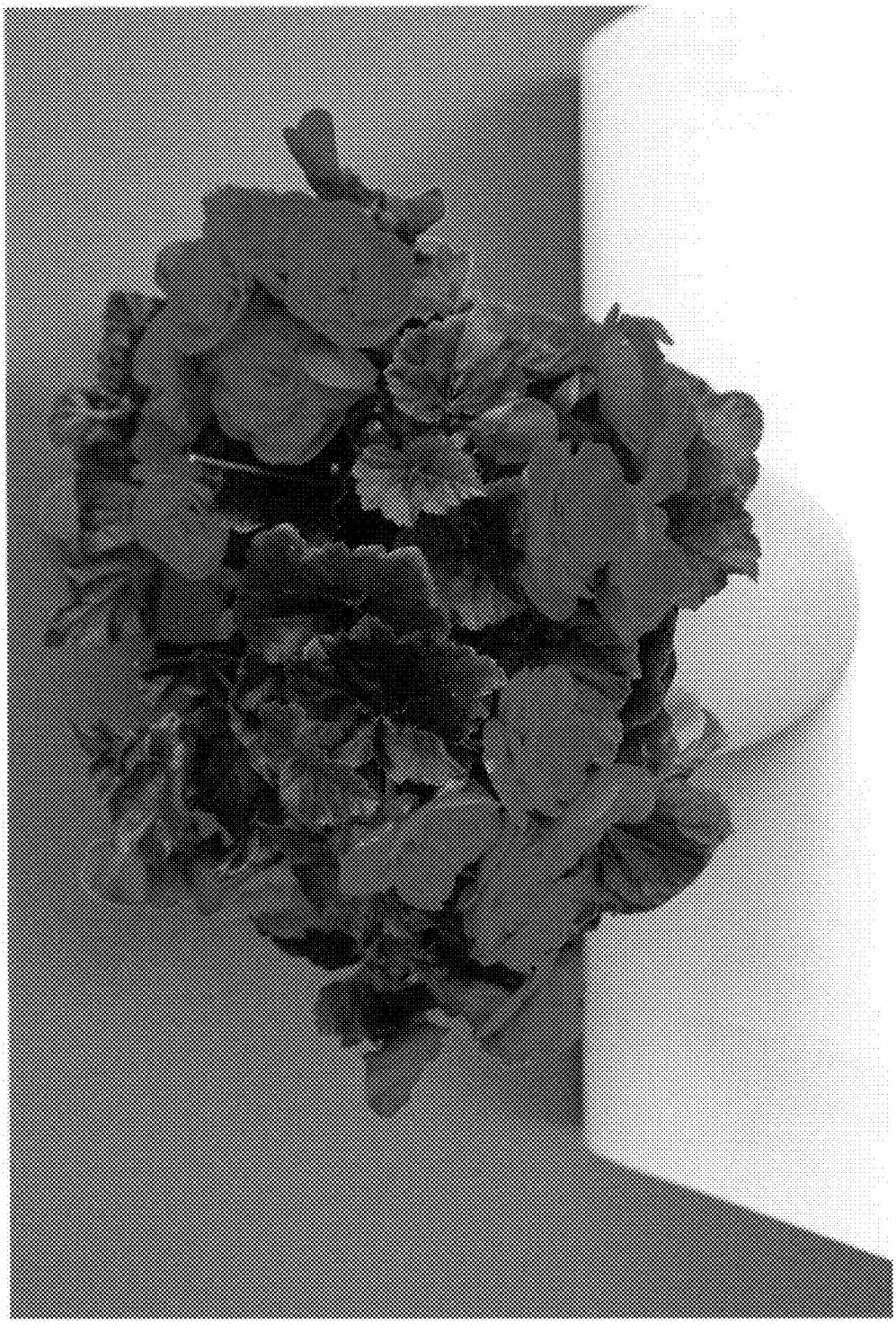

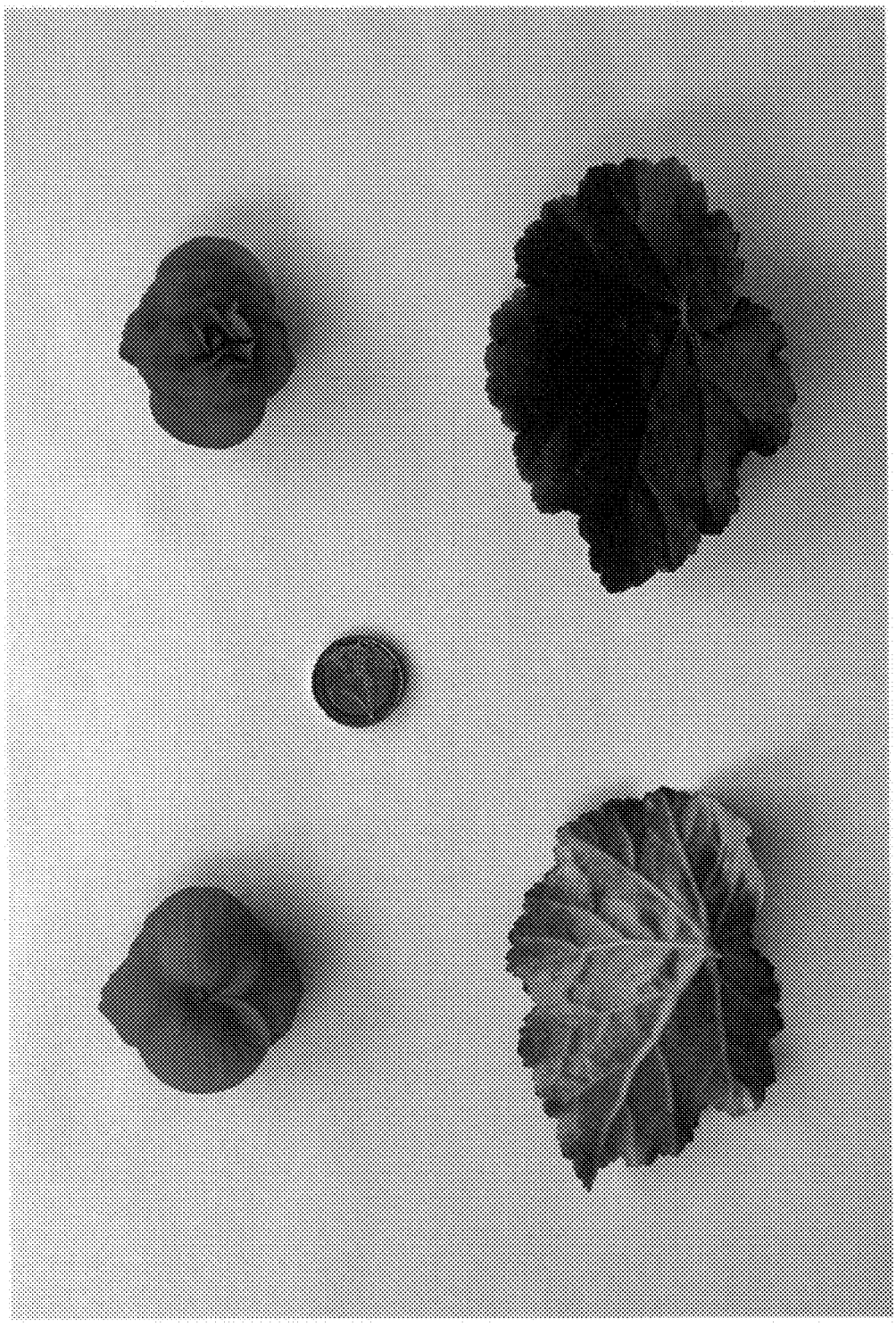

* * * * *